United States Patent
Sartori et al.

[11] Patent Number: 5,866,596
[45] Date of Patent: Feb. 2, 1999

[54] 3,4-DIARYLOXAZOLONE DERIVATIVES, THEIR METHODS OF PREPARATION AND THEIR USES IN THERAPEUTICS

[75] Inventors: Eric Sartori, Paris; Jean-Marie Teulon, La Celle Saint Cloud, both of France

[73] Assignee: Laboratories UPSA, Agen, France

[21] Appl. No.: 822,520

[22] Filed: Mar. 24, 1997

[30] Foreign Application Priority Data

Sep. 13, 1996 [FR] France .................................. 96 11188

[51] Int. Cl.[6] .................................................. A61K 31/42
[52] U.S. Cl. .................... 514/376; 514/30; 546/271.4; 548/232; 556/428; 568/31; 568/41; 568/55
[58] Field of Search .............. 548/232; 514/376

[56] References Cited

U.S. PATENT DOCUMENTS

| | | | |
|---|---|---|---|
| 3,895,024 | 7/1975 | Hafeci | 548/229 |
| 4,001,228 | 1/1977 | Mattacia | 548/232 |
| 4,186,129 | 1/1980 | Huth et al. | 548/232 |
| 4,632,930 | 12/1986 | Carini | 548/235 |
| 4,824,838 | 4/1989 | Wachtel | 548/232 |
| 5,380,738 | 1/1995 | Norman et al. | 548/235 |
| 5,474,995 | 12/1995 | Ducharme et al. | 514/374 |
| 5,643,933 | 7/1997 | Talley et al. | 514/374 |

FOREIGN PATENT DOCUMENTS

96/36617  11/1996  WIPO .

*Primary Examiner*—Donald G. Daus
*Attorney, Agent, or Firm*—Barry J. Marenberg

[57] ABSTRACT

The present invention relates to the derivatives of formula:

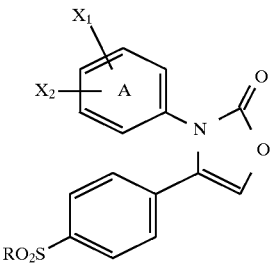

and to their use in therapeutics, especially as drugs with anti-inflammatory and analgesic properties.

12 Claims, No Drawings

3,4-DIARYLOXAZOLONE DERIVATIVES, THEIR METHODS OF PREPARATION AND THEIR USES IN THERAPEUTICS

The present invention relates to the 3,4-diaryloxazolone derivatives of general formula (I) as novel products.

One of the arachidonic acid biotransformation pathways is the cyclooxygenase pathway, which makes it possible to transform arachidonic acid to PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis which can give rise to side effects. The inhibition of COX-2 will cause a decrease in the prostaglandins produced in an infammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated in the treatment of inflammatory phenomena and in the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated in the treatment of bronchial asthma, dysmenorrhea, tendinitis, bursitis, dermatological inflammations such as psoriasis, eczema, burns and dermatitis. They can also be used in the treatment of gastrointestinal inflammations, Crohn's disease, gastritis and ulcerative colitis.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the method for the preparation of the said products and to their application in therapeutics.

These 3,4-diaryloxazolone derivatives have the general formula (I):

Formula (I)

in which:

R is:
a lower alkyl radical having 1 to 6 carbon atoms, or
an —$NH_2$ group.
A is:
a phenyl ring, or
a pyridine ring,
$X_1$ and $X_2$ independently are:
the hydrogen atom,
a halogen atom,
a lower alkyl radical having 1 to 6 carbon atoms, or
- a trifluoromethyl radical.

In the description and the claims, <<lower alkyl>> is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

<<Halogen>> is understood as meaning a chlorine, bromine, iodine or fluorine atom.

The derivatives according to the invention are advantageously the derivatives of formula (I) above in which:
R is a lower alkyl radical having 1 to 6 carbon atoms,
A is a phenyl ring,
$X_1$ and $X_2$ independently are:
the hydrogen atom,
a halogen atom,
a lower alkyl radical having 1 to 6 carbon atoms, or
a trifluoromethyl radical.

Within the framework of the present invention, it will be advantageous to use a compound of formula (I) in which at least one of the following conditions is satisfied:
R is a methyl radical,
A is a phenyl ring,
$X_1$ is a fluorine or chlorine atom or a methyl radical, and
$X_2$ is the hydrogen atom or a chlorine atom.

The particularly preferred compounds of the invention are as follows:
3-(4-fluorophenyl)-4-(4-methanesulfonylphenyl)-3H-oxazol-2-one 3-(4-chlorophenyl)-4-(4-methanesulfonylphenyl)-3H-oxazol-2-one 3-(3-methylphenyl)-4-(4-methanesulfonylphenyl)-3H-oxazol-2-one

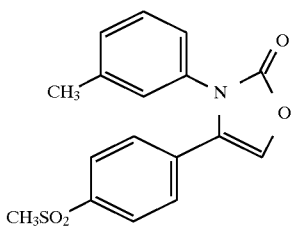

3-(3-chlorophenyl)-4-(4-methanesulfonylphenyl)-3H-oxazol-2-one

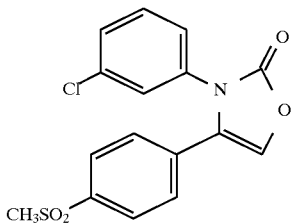

3-(3,4-dichlorophenyl)-4-(4-methanesulfonylphenyl)-3H-oxazol-2-one

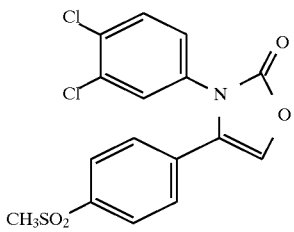

The compounds of the invention of formula (I) can be obtained by a cyclisation of derivatives of formula (II):

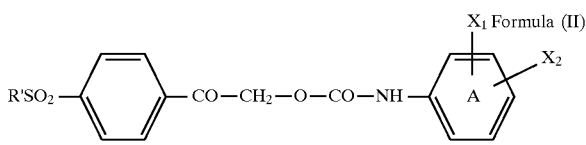

in which A, $X_1$ and $X_2$ are as defined above, and R' is a lower alkyl radical having 1 to 6 carbon atoms, by heating in a solvent such as dimethoxyethane or in an acid such as acetic acid or propionic acid.

The compounds of formula (I) of the invention wherein R is an —$NH_2$ group can be obtained from corresponding compounds of formula (I), in which R is the methyl group, by any method which transforms a methanesulfone group into a sulfonamide group, these methods being known to persons of the art and being described in the literature, such as, for example that described in Tetrahedron Letters, 1994, 39(35), 7201 which consists in reacting a methanesulfone with a base and a trialkylborane in an organic solvent such as tetrahydrofuran under reflux, followed by the action of hydroxylamine O-sulfonic acid.

The compounds of formula (II) are obtained by the reaction of an isocyanate of formula (III):

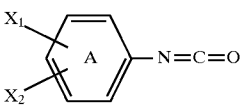

in which A, $X_1$ and $X_2$ have the same meaning as above, with 2-hydroxy-1-[4-methanesulfonylphenyl]ethanone of formula (IV):

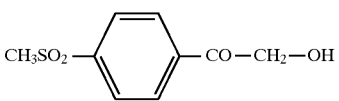

by heating in a solvent such as toluene or acetonitrile, in the presence or not of a base such as pyridine or triethylamine.

The isocyanates of formula (III) are commercially available or can be synthesised according to methods known to persons of the art.

One of these methods consists in reacting phosgene or a phosgene precursor with a compound of formula (V)

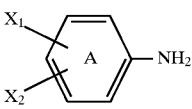

in which A, $X_1$ and $X_2$ are as defined above, for example according to the method described in the reference Twitchett, Chem. Soc. Rev., 1974, 3, 209–230.

Another method consists in reacting an acid chloride with sodium azide, for example according to the method described in the reference: Organic Syntheses Collective Volume 3, p 846.

2-hydroxy-1-[4-methanesulfonylphenyl]ethanone of formula (IV) can be prepared in different ways.

A first synthetic route includes the oxidation of 2-hydroxy-1-[4-methylthiophenyl]ethanone with the aid of meta-chloroperbenzoic acid in a solvent such as dichloromethane. The starting 2-hydroxy-1-[4-methylthiophenyl]ethanone can be obtained, for example by the action of potassium formate on 2-bromo-1-[4-methylthiophenyl]ethanone by heating in a solvent such as methanol, a mixture of methanol and acetone, or dimethylformamide, followed by hydrolysing the product obtained, the bromo-ketone being itself obtained by bromination of 4-methylthioacetophenone with the aid of bromine. This first route can be represented by the following scheme:

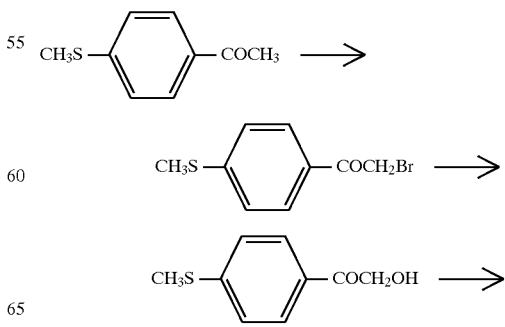

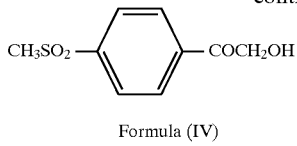

Formula (IV)

A second synthetic route to the hydroxy-ketone of formula (IV) consists in oxidising 4-methylthioacetophenone with meta-chloroperbenzoic acid in dichloromethane, followed by brominating the ketone thus obtained with bromine, before replacing the bromine atom by a hydroxyl group using, for example, potassium formate as before, according to the following scheme:

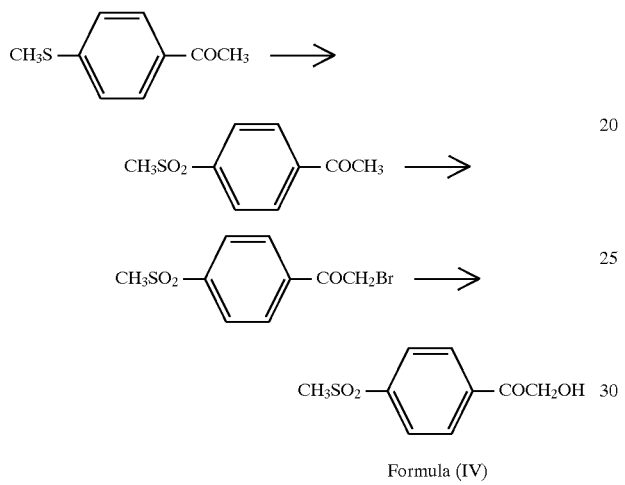

Formula (IV)

A third synthetic route to the hydroxy-ketone of formula (IV) consists in preparing 1-methylthio-4-[1-[(trimethylsilyl)oxy]ethenyl]benzene by the action of chlorotrimethylsilane on 4-methylthioacetophenone in the presence of triethylamine and sodium iodide in acetonitrile; this derivative being then oxidised to 2-hydroxy-1-[4-methanesulfonylphenyl]ethanone of formula (IV) with the aid of meta-chloroperbenzoic acid in dichloromethane, according to the following scheme:

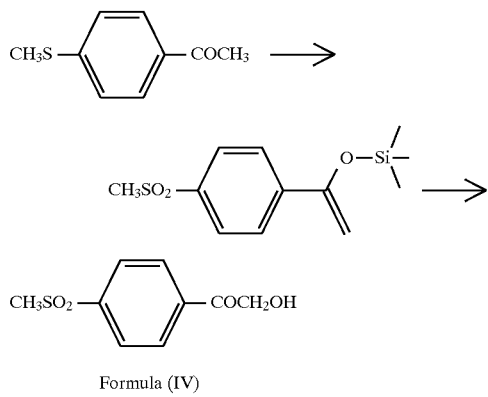

Formula (IV)

The compounds of formula (I) as defined above are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above.

Thus the invention also covers a pharmaceutical composition characterised in that it comprises a pharmaceutically effective amount of at least one compound of formula (I) as defined above, incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatin capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above, can be incorporated therein together with excipients normally employed in pharmaceutical compositions, such as talc, gum arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavourings and colours.

The invention also covers a pharmaceutical composition with anti-inflammatory and analgesic activity which can be used especially as a favourable treatment for inflammatory phenomena and pain, the said composition comprising a pharmaceutically effective amount of at least one compound of formula (I) above, incorporated in a pharmaceutically acceptable excipient, vehicle or carrier.

In one embodiment, a pharmaceutical composition with anti-inflammatory and analgesic activity is prepared which may be used especially as a favourable treatment for various inflammations and pain.

In one variant, a composition is formulated as gelatin capsules or tablets containing a dose of 1 mg to 1000 mg, or as injectable preparations containing a dose of 0.1 mg to 500 mg. It is also possible to use compositions formulated as suppositories, oinments, creams, gels, aerosol preparations, transdermal preparations or plasters.

The invention also covers a method of therapeutic treatment for mammals, wherein a therapeutically effective amount of at least one compound of formula (I) as defined above is administered to the said mammal. In one variant of this method of treatment, the compound of formula (I) either by itself or in association with a pharmaceutically acceptable excipient, is formulated as gelatin capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favourable treatment for inflammatory phenomena and pain.

In human and animal therapeutics, the compounds of formula (I) can be administered, by themselves or in association with a physiologically acceptable excipient, in any form, in particular orally in the form of gelatin capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatin capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly from the following Examples, which in no way imply a limitation but are given by way of illustration.

EXAMPLE 1

2-hydroxy-1-[4-methylthiophenyl]ethanone 119 g of 2-bromo-1-[4-methylthiophenyl]ethanone (prepared according to J. Amer. Chem. Soc., 1952, p. 5475) are dissolved in a mixture of 200 ml of methanol and 300 ml of acetone. 53 g of potassium formate are added and the mixture is heated under reflux for 4 hours. The organic solvents are evaporated, the residual oil is taken up with ethyl acetate and washed with a saturated solution of sodium chloride. The ethyl acetate is evaporated and the residual oil crystallises in isopropyl ether.

Yield 41g, 46%, melting point: 102° C.

EXAMPLE 2

2-hydroxy-1-[4-methanesulfonylphenyl]ethanone

Formula (IV)

41 g of product of Example 1 are dissolved in 1 l of dichloromethane. 116 g of meta-chloroperbenzoic acid are added portionwise. The reaction mixture is stirred at room temperature for 3 hours, then 38.8 g of meta-chloroperbenzoic acid are added. After 1 hour the insoluble material is filtered, the organic phase is washed with a saturated solution of sodium bicarbonate, then dried and evaporated. The beige solid obtained is taken up with isopropanol and filtered, providing 38 g of expected product.

Yield 79%, melting point: 116° C.

EXAMPLE 3

2-(4-methanesulfonylphenyl)-2-oxo-ethyl 4-fluorophenyl-carbamate

Formula (II) A=phenyl, $X_1$=4-F, $X_2$=H, R'=$CH_3$ 3.4 g of the product of Example 2 and 1.8 ml of 4-fluorophenylisocyanate are dissolved in 30 ml of anhydrous toluene and heated under reflux for 2 hours. 0.6 ml of 4-fluorophenylisocyanate are then added and the reaction medium is once again heated under reflux for 8 hours. The precipitate formed is then filtered, then washed with methanol, then with pentane. 2.9 g of a product melting at 191° C. are obtained.

Yield 52%.

EXAMPLE 4

3-(4-fluorophenyl)-4-(4-methanesulfonylphenyl)-3H-oxazol-2-one

Formula (I): A=phenyl, $X_1$=4-F, $X_2$=H, R=$CH_3$ 2.9 g of the product of Example 3 are dissolved in 15 ml of acetic acid and are heated under reflux for 12 hours. The acetic acid is evaporated, the residual oil is taken up with dichloromethane and washed with an aqueous solution of bicarbonate. The organic phase is dried and evaporated and the crude product obtained is chromatographed on a silica gel column, (eluent: ethyl acetate:cyclohexane, 50:50). The fractions containing the major product are evaporated and the solid obtained is crystallised from isopropyl alcohol, washed with pentane and dried to provide 1.4 g of expected product.

Yield 51%, melting point 151.1° C.

EXAMPLE 5

2-(4-methanesulfonylphenyl)-2-oxoethyl (2-trifluoromethylphenyl)carbamate

Formula (II): A=phenyl, $X_1$=2-$CF_3$, $X_2$=H, R'=$CH_3$ 5 g of the product of Example 2 and 3.3 ml of 2-trifluoromethylphenylisocyanate are dissolved in 100 ml of anhydrous acetonitrile. 5 drops of pyridine are added and the reaction mixture is heated under reflux for 4 hours. The acetonitrile is evaporated and 9 g of an oil are obtained which are used as such in the next step.

EXAMPLE 6

3-(2-trifluoromethylphenyl)-4-(4-methanesulfonylphenyl)-3H-oxazol-2-one

Formula (I): A=phenyl, $X_1$=2-$CF_3$, $X_2$=H, R=$CH_3$ 9 g of the product of Example 5 are dissolved in 170 ml of acetic acid and heated under reflux for 6 hours. The acetic acid is evaporated and replaced with propionic acid. The reaction mixture is heated for 18 hours in the propionic acid, then the propionic acid is evaporated. The residue is taken up with dichloromethane and washed with a solution of sodium bicarbonate. The organic phase is dried and evaporated, and the oil obtained is chromatographed on a silica gel column (eluent: ethyl acetate:cyclohexane, 50:50 then 70:30). The fractions containing the major product are concentrated and the solid obtained is taken up with ether and filtered to provide 1.4 g of desired product (yield 16%). Melting point: 187° C.

The Examples 7 to 15 are non isolated intermediate products (of Formula II) obtained according to a preparation identical to that in Example 5.

EXAMPLE 7

2-(4-methanesulfonylphenyl)-2-oxoethyl phenylcarbamate

Formula (II): A=phenyl, $X_1$=$X_2$=H, R'=$CH_3$.

EXAMPLE 8

2-(4-methanesulfonylphenyl)-2-oxoethyl (4-chlorophenyl)-carbamate

Formula (II): A=phenyl, $X_1$=4-Cl, $X_2$=H, R'=$CH_3$.

EXAMPLE 9

2-(4-methanesulfonylphenyl)-2-oxoethyl (3-methylphenyl)-carbamate

Formula (II): A=phenyl, $X_1$=3-$CH_3$, $X_2$=H, R'=$CH_3$.

EXAMPLE 10

2-(4-methanesulfonylphenyl)-2-oxoethyl (3-chlorophenyl)-carbamate

Formula (II): A=phenyl, $X_1$=3-Cl, $X_2$=H, R'=$CH_3$.

EXAMPLE 11

2-(4-methanesulfonylphenyl) -2-oxoethyl (3,4-dichlorophenyl)-carbamate

Formula (II): A=phenyl, $X_1$=3-Cl, $X_2$=4-Cl, R'=$CH_3$.

EXAMPLE 12

2-(4-methanesulfonylphenyl)-2-oxoethyl (3-fluorophenyl)-carbamate

Formula (II): A=phenyl, $X_1$=3-F, $X_2$=H, R'=$CH_3$.

EXAMPLE 13

2-(4-methanesulfonylphenyl)-2-oxoethyl (4-trifluoromethylphenyl)carbamate

Formula (II): A=phenyl, $X_1$=4-$CF_3$, $X_2$=H, R'=$CH_3$.

EXAMPLE 14

2-(4-methanesulfonylphenyl)-2-oxoethyl (2-chlorophenyl)-carbamate

Formula (II): A=phenyl, $X_1$=2-Cl, $X_2$=H, R'=$CH_3$

EXAMPLE 15

2-(4-methanesulfonylphenyl)-2-oxoethyl (4-methylphenyl)-carbamate

Formula (II): A=phenyl, $X_1$=4-$CH_3$, $X_2$=H, R'=$CH_3$.

The products of formula (I) of Examples 16 to 24 have been obtained from the products of Examples 7 to 15 according to the method of Example 4.

EXAMPLE 16

3-phenyl-4-(4-methanesulfonylphenyl)-3H-oxazol-2-one

Formula (I): A=phenyl, $X_1$=$X_2$=H, R=$CH_3$.
Melting point: 210° C.

EXAMPLE 17

3-(4-chlorophenyl)-4-(4-methanesulfonylphenyl)-3H-oxazol-2-one

Formula (I): A=phenyl, $X_1$=4-Cl, $X_2$=H, R=$CH_3$.
Melting point: 194° C.

EXAMPLE 18

3-(3-methylphenyl)-4-(4-methanesulfonylphenyl)-3H-oxazol-2-one

Formula (I): A=phenyl, $X_1$=3-$CH_3$, $X_2$=H, R=$CH_3$.
Melting point: 191° C.

EXAMPLE 19

3-(3-chlorophenyl)-4-(4-methanesulfonylphenyl)-3H-oxazol-2-one

Formula (I): A=phenyl, $X_1$=3-Cl, $X_2$=H, R=$CH_3$.
Melting point: 185° C.

EXAMPLE 20

3-(3,4-dichlorophenyl)-4-(4-methanesulfonylphenyl)-3H-oxazol-2-one

Formula (I): A=phenyl, $X_1$=3-Cl, $X_2$=4-Cl, R=$CH_3$.
Melting point: 192° C.

EXAMPLE 21

3-(3-fluorophenyl)-4-(4-methanesulfonylphenyl)-3H-oxazol-2-one

Formula (I): A=phenyl, $X_1$=3-F, $X_2$=H, R=$CH_3$.
Melting point: 143° C.

EXAMPLE 22

3-(4-methylphenyl)-4-(4-methanesulfonylphenyl)-3H-oxazol-2-one

Formula (I): A=phenyl, $X_1$=4-$CH_3$, $X_2$=H, R=$CH_3$.
Melting point: 204° C.

EXAMPLE 23

3-(4-trifluoromethylphenyl)-4-(4-methanesulfonylphenyl)-3H-oxazol-2-one

Formula (I): A=phenyl, $X_1$=4-$CF_3$, $X_2$=H, R=$CH_3$
Melting point: 198° C.

EXAMPLE 24

3-(2-chlorophenyl)-4-(4-methanesulfonylphenyl)-3H-oxazol-2-one

Formula (I): A=phenyl, $X_1$=2-Cl, $X_2$=H, R=$CH_3$
Melting point: 162° C.

PHARMACOLOGY

The anti-inflammatory activity of the compounds of the Examples has been evaluated according to the method of oedema with carrageenan and the analgesic activity has been evaluated according to the method of arthritis with kaolin.

Methods

Anti-inflammatory activity:

The anti-inflammatory activity is evaluated in rats by the test of oedema with carrageenan. The product is administered orally at a rate of 2.5 ml/100 g (n=6 animals per dose) 2 hours 30 minutes after a water overload taken orally (2.5 ml/100 g). One hour after administration of the product, the oedema is induced by plantar subcutaneous injection of aqueous 2% carrageenan solution. The percentage inhibition of the volume of the oedema is calculated after 3 hours by measuring the volume of the paw with the aid of a mercury plethysmometer.

Analgesic activity:

The analgesic activity is evaluated in rats by the test of arthritis with kaolin. Thirty minutes after intra-articular administration of an aqueous 10% suspension of kaolin, the product is administered orally at a rate of 1 ml/100 g (n=10 animals per dose). The percentage inhibition of the animal's pain response (by rating the way it walks) is calculated 5 hours 30 minutes after administration of the product.

| Example | Anti-inflammatory activity % inhibition (30 mg/kg) | Analgesic activity % inhibition (30 mg/kg) |
|---|---|---|
| 4 | 53 | 55 |
| 16 | 45 | 60 |
| 17 | 32 | 42 |
| 18 | 18 | 0 |
| 19 | 37 | 60 |

-continued

| Example | Anti-inflammatory activity % inhibition (30 mg/kg) | Analgesic activity % inhibition (30 mg/kg) |
|---|---|---|
| 20 | 48 | 75 |
| 21 | 55 | not determined |
| 22 | 42 | not determined |

Inhibition of the COX-1 and COX-2 enzymatic activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 $\mu$M for COX-1, 4 $\mu$M for COX-2) is added to the reaction medium and incubation is carried out for 5 minutes at 25° C. When incubation has ended, the enzymatic reaction is stopped by the addition of 1N HCl and the PGE2 produced is determined by EIA.

The results are expressed as the percentage inhibition of the COX-1 and COX-2 enzymatic activities and correspond to mean (±) standard deviations from the average of 4 determinations.

| Example | % inhibition of COX-2 activity | | % inhibition of COX-1 activity | |
|---|---|---|---|---|
| | $10^{-5}$ M | $10^{-7}$ M | $10^{-5}$ M | $10^{-7}$ M |
| 4 | 82.7 | 12 | 0 | 0 |
| 16 | 78 | 16 | 0 | 0 |
| 17 | 85 | 11 | 0 | 0 |
| 18 | 92 | 14 | 0 | 0 |
| 19 | 87 | 18 | 0 | 0 |
| 20 | 94 | 26 | 0 | 0 |
| 21 | 76 | 11 | 0 | 0 |
| 22 | 88 | 12 | | |

TOLERANCE

Gastric tolerance:

The gastic tolerance study is carried out in Charles River rats strain CD weighing 110 to 150 g. The animals are placed on a water diet 24 hours before administration of the product or the vehicle alone, via the oral route (1 ml/100 g) (n=6 animals per dose). Six hours after administration, the animals are sacrificed and the stomachs are removed and opened along the greater curvature. The number of haemorrhagic spots and lines per stomach identified macroscopically permits establishing an ulceration index (0: no lesion, 1: 1 to 2 lesions, 2: 3 to 4 lesions, 3: 5 to 8 lesions, 4: 9 to 16 lesions, 5: more than 17 lesions) and estimating the 50% ulcerogenic dose ($UD_{50}$=dose expressed in mg/kg inducing 4 to 5 lesions).

| Example | $UD_{50}$ (confidence limit) mg/kg |
|---|---|
| 4 | >300 |
| indomethacin | 8.3 (5.8–11.8) |

TOXICOLOGY

The first toxicology studies performed show that the products of the Examples do not induce a deleterious effect in the rat after the oral absorption of doses ranging up to 300 mg/kg.

What is claimed is:

1. A 3,4-diaryloxazolone compound of formula (I):

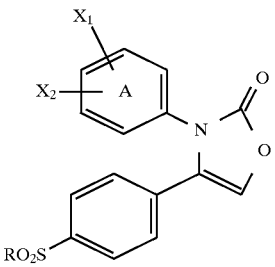

Formula (I)

wherein:

R is:
   a lower alkyl radical having 1 to 6 carbon atoms, or
   an $NH_2$ group A is:
   a phenyl ring, $X_1$ and $X_2$ independently are:
   the hydrogen atom,
   a halogen atom,
   a lower alkyl radical having 1 to 6 carbon atoms, or
   a trifluormethyl radical.

2. A compound of formula (I) according to claim 1, wherein:

R is a lower alkyl radical having 1 to 6 carbon atoms,

A is a phenyl ring, $X_1$ and $X_2$ independently are:
   the hydrogen atom,
   a fluorine atom atom and a chlorine atom,
   a lower alkyl radical having 1 to 6 carbon atoms, or
   a trifluoromethyl radical.

3. A compound according to claim 1 wherein R is the methyl radical.

4. A compound according to claim 1 wherein $X_1$ is selected from the group consisting of the fluorine atom, the chlorine atom and a methyl radical and $X_2$ is the hydrogen atom.

5. A compound according to claim 1 wherein $X_1$ and $X_2$ are the chlorine atom.

6. A compound according to claim 1 which is selected from the group consisting of:

3-(4-fluorophenyl)-4-(4-methanesulfonylphenyl)-3H-oxazol-2-one

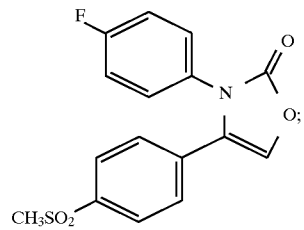

3-(4-chlorophenyl)-4-(4-methanesulfonylphenyl)-3H-oxazol-2-one

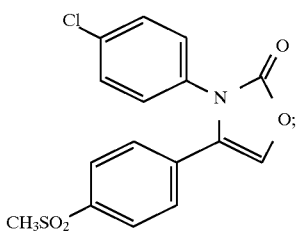

3-(3-methylphenyl)-4-(4-methanesulfonylphenyl)-3H-oxazol-2-one

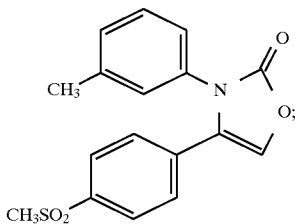

3-(3-chlorophenyl)-4-(4-methanesulfonylphenyl)-3H-oxazol-2-one

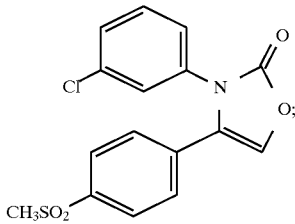

and 3-(3,4-dichlorophenyl)-4-(4-methanesulfonylphenyl)-3H-oxazol-2-one

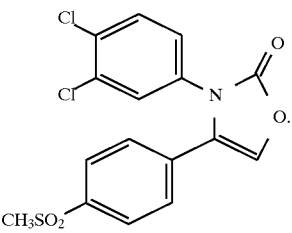

7. A pharmaceutical composition which comprises a pharmaceutically effective amount of a compound of formula (I) as defined in claim 1 incorporated in a pharmaceutically acceptable excipient, vehicle or carrier.

8. A pharmaceutical composition with anti-inflammatory and analgesic activity which comprises a pharmaceutically effective amount of a compound of formula (I) as defined in claim 1 incorporated in a pharmaceutically acceptable excipient, vehicle or carrier.

9. A pharmaceutically acceptable composition according to claim 7 which is presented in the form of gelatin capsules or tablets containing a dose of 1 mg to 1,000 mg.

10. A pharmaceutically acceptable composition according to claim 7 which is presented in the form of injectable preparations containing a dose of 0.1 mg to 500 mg.

11. A method for the treatment of inflammation in a mammal which comprises administering an effective amount of a compound of formula I as defined in claim 1 to the said mammal.

12. A method for the treatment of pain in a mammal which comprises administering an effective amount of a compound of formula I as defined in claim 1 to the said mammal.

* * * * *